(12) United States Patent
Dubief et al.

(10) Patent No.: US 6,471,952 B1
(45) Date of Patent: Oct. 29, 2002

(54) COSMETIC COMPOSITION INCLUDING AT LEAST ONE SILICONE-GRAFTED POLYMER AND AT LEAST ONE COMBINATION OF AN ANIONIC POLYMER AND A CATIONIC POLYMER

(75) Inventors: Claude Dubief, Le Chesnay (FR); Daniele Cauwet-Martin, Paris (FR); Christine Dupuis, Paris (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 08/983,338

(22) PCT Filed: Sep. 16, 1996

(86) PCT No.: PCT/FR96/01439

§ 371 (c)(1),
(2), (4) Date: Dec. 30, 1997

(87) PCT Pub. No.: WO97/12588

PCT Pub. Date: Apr. 10, 1997

(30) Foreign Application Priority Data

Sep. 29, 1995 (FR) .............................................. 95 11486

(51) Int. Cl.[7] .............................................. A61K 7/075
(52) U.S. Cl. .............................. 424/70.12; 424/70.122; 424/501
(58) Field of Search .............................. 424/401, 70.12, 424/70.122, 70.16, 70.17, DIG. 1–2, 47, 484, 486–87, 501; 510/122; 514/881, 744–745

(56) References Cited

U.S. PATENT DOCUMENTS

| | | | |
|---|---|---|---|
| 4,724,851 A | 2/1988 | Cornwall et al. | 132/7 |
| 5,362,485 A | 11/1994 | Hayama et al. | 424/70 |

FOREIGN PATENT DOCUMENTS

| | | |
|---|---|---|
| EP | 0 412 710 | 2/1991 |
| EP | 0 636 361 | 2/1995 |
| FR | 0 524 612 | 1/1993 |
| FR | 2 709 954 | 3/1995 |
| JP | 6-92825 | 7/1992 |
| WO | WO 91/15186 | 10/1991 |
| WO | WO 95/00108 | 1/1995 |
| WO | WO 95/05800 | 3/1995 |

Primary Examiner—Edward J. Webman
(74) Attorney, Agent, or Firm—Finnegan, Henderson, Farabow, Garrett & Dunner, LLP

(57) ABSTRACT

A cosmetic or dermatological composition for treating keratinous material, particularly hair, including a cosmetically or dermatologically acceptable medium containing as least one silicone-grafter polymer with a polysiloxane portion and a portion consisting of a non-silicone organic chain, wherein one of the two portions constitutes the main polymeric chain while the other is grafted onto said main chain, and at least one combination of at least one anionic polymer and at least one cationic polymer. Such compositions are particularly suitable for use as rinsable or non-rinsable products for washing and conditioning hair, hair setting, or hair styling.

63 Claims, No Drawings

COSMETIC COMPOSITION INCLUDING AT LEAST ONE SILICONE-GRAFTED POLYMER AND AT LEAST ONE COMBINATION OF AN ANIONIC POLYMER AND A CATIONIC POLYMER

The present invention relates to a cosmetic or dermatological composition comprising at least one grafted silicone polymer and at least one combination of an anionic polymer and a cationic polymer.

Grafted silicone polymers are known in the prior art, such as those described in patent applications EP-A-0,412,704, EP-A-0,412,707, EP-A-0,640,105, WO 95/00578, EP-A-0,582,152 and WO 93/23009. These polymers are proposed in particular in haircare products for their styling properties. However, when these polymers are used, the fixing power of the composition and the feel of the hair are unsatisfactory.

The expression fixing power of the composition will be understood to denote the ability of this composition to give the hair cohesion such that the initial shape of the hairstyle is held.

It is sought to obtain cosmetic compositions which are capable of giving the hair styling, volume, shaping and holding properties while at the same time having good cosmetic properties such as softness, feel or disentangling.

The Applicant has discovered, surprisingly, that by combining at least one grafted silicone polymer with at least one combination of an anionic polymer and a cationic polymer, cosmetic properties such as the softness and feel of the hair are substantially superior to those obtained with the grafted silicone polymer used alone or with the combination of an anionic polymer and a cationic polymer.

The composition according to the invention is thus essentially characterized in that it contains, in a cosmetically or dermatologically acceptable medium, at least one grafted silicone polymer comprising a polysiloxane portion and a portion consisting of a non-silicone organic chain, one of the two portions constituting the main chain of the polymer, the other being grafted onto the said main chain, and at least one combination of at least one anionic polymer and at least one cationic polymer.

The grafted silicone polymers according to the invention are preferably chosen from polymers having a non-silicone organic skeleton grafted with monomers containing a polysiloxane, polymers having a polysiloxane skeleton grafted with non-silicone organic monomers and mixtures thereof.

In the following text, in accordance with what is generally accepted, the term silicone or polysiloxane is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding $\equiv$Si—O—Si$\equiv$), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy radicals or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

In the following text, in accordance with what is generally accepted, the expression "polysiloxane macromer" is understood to refer to any monomer containing a polysiloxane-type polymer chain in its structure.

The polymers containing a non-silicone organic skeleton grafted with monomers containing a polysiloxane, in accordance with the present invention, consist of an organic main chain formed from organic monomers containing no silicone, on which is grafted, inside the said chain and optionally on at least one of its ends, at least one polysiloxane macromer.

The non-silicone organic monomers constituting the main chain of the grafted silicone polymer can be chosen from monomers containing ethylenic unsaturation which are polymerizable via a radical route, monomers which are polymerizable by polycondensation, such as those forming polyamides, polyesters or polyurethanes, and monomers which involve ring opening, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578. These are copolymers obtained by radical polymerization starting with monomers containing ethylenic unsaturation and silicone macromers having a terminal vinyl group, or alternatively copolymers obtained by reaction of a polyolefin comprising functionalized groups and a polysiloxane macromer having a terminal function which is reacted with the said functionalized groups.

One particular family of silicone polymers which is suitable for carrying out the present invention consists of silicone grafted copolymers comprising:

a) from 0 to 98% by weight of at least one lipophilic monomer (A) of low lipophilic polarity containing ethylenic unsaturation, which is polymerizable via a radical route;

b) from 0 to 98% by weight of at least one polar hydrophilic monomer (B) containing ethylenic unsaturation, which is copolymerizable with the (A)-type monomer(s);

c) from 0.01 to 50% by weight of at least one polysiloxane macromer (C) of general formula:

$$X(Y)_nSi(R)_{3-m}Z_m \qquad (I)$$

where:
X denotes a vinyl group which is copolymerizable with the monomers (A) and (B);
Y denotes a divalent bonding group;
R denotes a hydrogen, a $C_1$–$C_6$ alkyl or alkoxy or a $C_6$–$C_{12}$ aryl;
Z denotes a monovalent polysiloxane unit having a number-average molecular weight of at least 500;
n is 0 or 1 and m is an integer ranging from 1 to 3; the percentages being calculated relative to the total weight of the monomers (A), (B) and (C).

These polymers are described, along with processes for their preparation, in U.S. Pat. Nos. 4,693,935, 4,728,571 and 4,972,037 and in patent applications EP-A-0,412,704, EP-A-0,412,707 and EP-A-0,640,105. They have a number-average molecular weight preferably ranging from 10,000 to 2,000,000 and preferably a glass transition temperature Tg or a crystalline melting point Tm of at least −20° C.

As examples of lipophilic monomers (A), mention may be made of acrylic or methacrylic acid esters of $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; acrylic or methacrylic acid esters of 1,1-dihydroperfluoroalkanols or of homologues thereof; acrylic or methacrylic acid esters of ω-hydridofluoroalkanols; acrylic or methacrylic acid esters of fluoroalkylsulphoamido alcohols; acrylic or methacrylic acid esters of fluoroalkyl alcohols; acrylic or methacrylic acid esters of fluoroether alcohols; or mixtures thereof.

The preferred monomers (A) are chosen from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate and 2-(N-butylperfluorooctanesulphonamido)ethyl acrylate, and mixtures thereof.

As examples of polar monomers (B), mention may be made of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and semiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam, or mixtures thereof. The preferred monomers (B) are chosen from the group consisting of acrylic acid, N,N-dimethylacrylamide, dimethylaminoethyl methacrylate, quaternized dimethylaminoethyl methacrylate and vinylpyrrolidone, and mixtures thereof.

The preferred polysiloxane macromers (C) of formula (I) are chosen from those corresponding to the general formula (II) below:

(II)

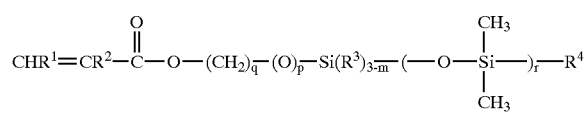

in which:
$R^1$ is hydrogen or —COOH (preferably hydrogen);
$R^2$ is hydrogen, methyl or —CH$_2$COOH (preferably methyl);
$R^3$ is $C_1$–$C_6$ alkyl, alkoxy, or alkylamino, $C_6$–$C_{12}$ aryl or hydroxyl (preferably methyl);
$R^4$ is $C_1$–$C_6$ alkyl, alkoxy or alkylamino, $C_6$–$C_{12}$ aryl or hydroxyl (preferably methyl);
q is an integer from 2 to 6 (preferably 3);
p is 0 or 1;
r is an integer from 5 to 700;
m is an integer from 1 to 3 (preferably 1).

The polysiloxane macromers of formula:

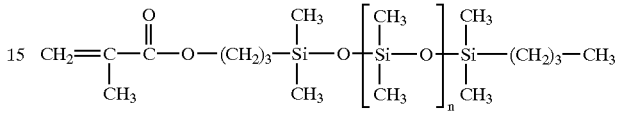

with n being an integer ranging from 5 to 700, are more particularly used.

One particular embodiment of the invention consists in using a copolymer which can be obtained by radical polymerization starting with the monomer mixture consisting of:
a) 60% by weight of tert-butyl acrylate;
b) 20% by weight of acrylic acid;
c) 20% by weight of silicone macromer of formula:

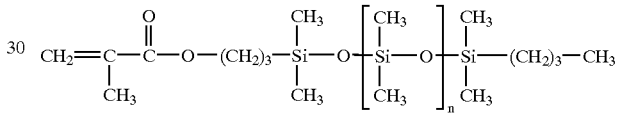

with n being an integer ranging from 5 to 700; the weight percentages being calculated relative to the total weight of the monomers.

Another particular embodiment of the invention consists in using a copolymer which can be obtained by radical polymerization starting with the monomer mixture consisting of:
a) 80% by weight of tert-butyl acrylate;
b) 20% by weight of silicone macromer of formula:

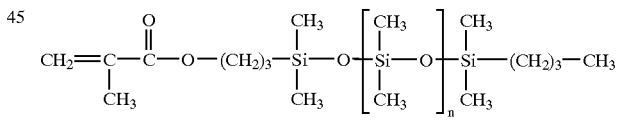

with n being an integer ranging from 5 to 700; the weight percentages being calculated relative to the total weight of the monomers.

Another particular family of grafted silicone polymers containing a non-silicone organic skeleton, which is suitable for carrying out the present invention, consists of silicone grafted copolymers which can be obtained by reactive extrusion of a polysiloxane macromer having a terminal reactive function, with a polyolefin-type polymer containing reactive groups which can react with the terminal function of the polysiloxane macromer in order to form a covalent bond allowing grafting of the silicone to the main chain of the polyolefin.

These polymers are described, along with a process for their preparation, in patent application WO 95/00578.

The reactive polyolefins are preferably chosen from polyethylenes or polymers of ethylene-derived monomers such as propylene, styrene, alkylstyrene, butylene, butadiene, (meth)acrylates, vinyl esters or equivalents, containing reactive functions which can react with the terminal function of the polysiloxane macromer. They are chosen more particularly from copolymers of ethylene or of ethylene derivatives and of monomers chosen from those containing a carboxylic function, such as (meth)acrylic acid; those containing an acid anhydride function such as maleic anhydride; those containing an acid chloride function such as (meth)acryloyl chloride; those containing an ester function such as (meth) acrylic acid esters; those containing an isocyanate function.

The silicone macromers are preferably chosen from polysiloxanes containing a functionalized group, at the end of the polysiloxane chain or close to the end of the said chain, chosen from the group consisting of alcohols, thiols, epoxy groups and primary and secondary amines, and more particularly from those corresponding to the general formula:

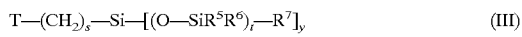

$$T-(CH_2)_s-Si-[(O-SiR^5R^6)_t-R^7]_y \qquad (III)$$

in which T is chosen from the group consisting of $NH_2$, NHR', an epoxy, OH, or SH function; $R^5$, $R^6$, $R^7$ and R', independently denote a $C_1$–$C_6$ alkyl, phenyl, benzyl, $C_6$–$C_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200,000 and more particularly from 9000 to 40,000.

According to the present invention, the grafted silicone polymer(s) containing a polysiloxane skeleton grafted with non-silicone organic monomers comprise a silicone (or polysiloxane ($\equiv$Si—O—)$_n$) main chain on which is grafted, inside the said chain as well as, optionally, on at least one of its ends, at least one organic group containing no silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio functional groups —SH with these same vinyl groups.

Examples of polymers with a polysiloxane skeleton grafted containing non-silicone organic monomers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer containing a polysiloxane skeleton grafted with non-silicone organic monomers, which is used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one, and preferably several, functional groups capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo) polymerization of at least one anionic monomer of unsaturated carboxylic acid type can, after reaction, be postneutralized with a base (sodium hydroxide, aqueous ammonia, and the like) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth) acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth) acrylate, tridecyl (meth)acrylate and stearyl (meth)acrylate, or mixtures thereof.

One family of silicone polymers containing a polysiloxane skeleton grafted with non-silicone organic monomers which is particularly suitable for carrying out the present invention consists of silicone polymers containing in their structure the unit of formula (IV) below:

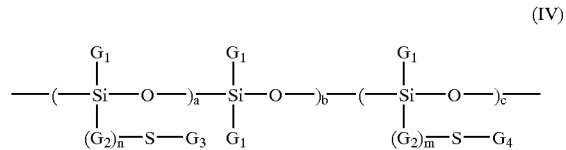

(IV)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (IV) above has at least one, and even more preferably all, of the following characteristics:

the radicals $G_1$ denote an alkyl radical, preferably the methyl radical;

n is non-zero and the radicals $G_2$ represent a divalent $C_1$–$C_3$ radical, preferably a propylene radical;

$G_3$ represents a polymeric radical resulting from the (homo)polymerization of at least one monomer of the carboxylic acid type containing ethylenic unsaturation, preferably acrylic acid and/or methacrylic acid;

$G_4$ represents a polymeric radical resulting from the (homo)polymerization of at least one monomer of the $C_1$–$C_{10}$ alkyl (meth)acrylate type, preferably of the isobutyl or methyl (meth)acrylate type.

Examples of silicone polymers corresponding to formula (IV) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of silicone polymers corresponding to formula (IV) are polydimethylsiloxanes (PDMS) on which are grafted, via a thiopropylene-type connecting chain, polymer units of the polyisobutyl (meth)acrylate type.

Preferably, the number-average molecular mass of the silicone polymers containing a polysiloxane skeleton grafted with non-silicone organic monomers, of the invention, ranges approximately from 10,000 to 1,000,000 and even more preferably approximately from 10,000 to 100,000.

The grafted silicone polymers in accordance with the invention are preferably used in an amount ranging from 0.01 to 20% by weight relative to the total weight of the composition. More preferably, this amount ranges from 0.1 to 15% by weight and even more particularly from 0.5 to 10% by weight.

According to the invention, any anionic polymer known per se can be used. Needless to say, one or more anionic polymers can be used.

Thus, the anionic polymers generally used are polymers containing groups derived from carboxylic, sulphonic or phosphoric acid and have a molecular weight of approximately between 500 and 5,000,000.

The carboxylic groups are provided by unsaturated mono. or dicarboxylic acid monomers such as those corresponding to the formula:

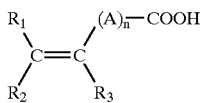

(V)

in which n is an integer from 0 to 10, A denotes a methylene group, optionally connected to the carbon atom of the unsaturated group, or to the neighbouring methylene group when n is greater than 1, via a hetero atom such as oxygen or sulphur, $R_1$ denotes a hydrogen atom or a phenyl or benzyl group, $R_2$ denotes a hydrogen atom or a lower alkyl or carboxyl group, $R_3$ denotes a hydrogen atom, a lower alkyl group or a —$CH_2$—COOH, phenyl or benzyl group. In the abovementioned formula, a lower alkyl radical preferably denotes a group having 1 to 4 carbon atoms and in particular methyl and ethyl.

The anionic polymers containing carboxylic groups which are preferred according to the invention A) Homo- or copolymers of acrylic or methacrylic acid salts thereof and in particular the products sold under the names Versicol E or K by the company Allied Colloid and Ultrahold by the company BASF. The copolymers of acrylic acid and of acrylamide sold in the form of their sodium salt under the names Reten 421, 423 or 425 by the company Hercules, the sodium silts of polyhydroxycarboxylic acids.

B) Copolymers of acrylic or methacrylic acids with a monoethylenic monomer such as ethylene, styrene, vinyl esters, acrylic acid esters or methacrylic acid esters, optionally grafted onto a polyalkylene glycol such as polyethylene glycol and optionally crosslinked. Such polymers are described in particular in French patent. 1,222,944 and German patent application 2,330,956, the copolymers of this type containing in their chain an optionally N-alkylated and/or hydroxyalkylated acrylamide unit as described in particular in Luxembourg patent applications 75370 and 75371 or sold under the name Quadramer by the company American Cyanamid. Mention may also be made of copolymers of acrylic acid and of $C_1$–$C_4$ alkyl methacrylate and terpolymers of vinylpyrrolidone, of acrylic acid and of methacrylate of $C_1$–$C_{20}$ alkyl, for example lauryl, such as the product sold by the company ISP under the name Acrylidone LM. Mention may also be made of the methacrylic acid and ethyl acrylate copolymer sold under the name Luvimer MAEX by the company BASF.

C) Copolymers derived from crotonic acid such as those containing vinyl acetate propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted and crosslinked, or alternatively a vinyl, allylic or methallylic ester of an α- or β-cyclic carboxylic acid. Such polymers are described, inter alia, in French patents 1,222,944, 1,580,545, 2,265,782, 2,265,781, 1,564,110 and 2,439,798. Commercial products falling into this class are the resins 28-29-30, 26-13-14 and 28-13-10 sold by the company National Starch.

D) Polymers derived from maleic, fumaric or itaconic acids or anhydrides with vinyl esters, vinyl ethers, vinyl halides, phenylvinyl derivatives or acrylic acid and its esters; these polymers can be esterified. Such polymers are described in particular in U.S. Pat. Nos. 2,047,398, 2,723,248 and 2,102, 113 and GB patent 839,805, and in particular those sold under the names Gantrez AN or ES by the company ISP.

Polymers which also fall within this category are the copolymers of maleic, citraconic or itaconic anhydride and of an allylic or methallylic ester optionally containing an acrylamide, methacrylamide or α-olefin group, acrylic or methacrylic esters, acrylic or methacrylic acid or vinylpyrrolidone in their chain; the anhydride functions are monoesterified or monoamidated. These polymers are described, for example, in French patents 2,350,384 and 2,357,241 by the applicant.

E) Polyacrylamides containing carboxylate groups.

The polymers comprising sulphonic groups are polymers containing vinylsulphonic, styrenesulphonic, naphthalenesulphonic or acrylamidoalkylsulphonic units.

These polymers can be chosen in particular from:

polyvinylsulphonic acid salts having a molecular weight of approximately between 1000 and 100,000, as well as the copolymers with an unsaturated comonomer such as acrylic or methacrylic acids and their esters, as well as acrylamide or its derivatives, vinyl ethers and vinylpyrrolidone;

polystyrenesulphonic acid salts, the sodium salts having a molecular weight of about 500,000 and about 100,000, which are sold respectively under the names Flexan 500 and Flexan 130 by National Starch. These compounds are described in patent FR 2,198,719;

polyacrylamidesulphonic acid salts, those mentioned in U.S. Pat. No. 4,128,631 and more particularly polyacrylamidoethylpropanesulphonic acid sold under the name Cosmedia Polymer HSP 1180 by Henkel.

According to the invention the anionic polymers are preferably chosen from acrylic acid copolymers such as the acrylic acid/ethyl acrylate/N-tert-butylacrylamidetryme sold under the name Ultrahold Strong by the company BASF, copolymers derived from crotonic acid such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acid or anhydride with vinyl esters, vinyl ethers, vinyl halides, phenylvinyl derivatives or acrylic acid and its esters, such as the methyl vinyl ether/maleic anhydride monoesterified copolymer sold, for example, under the name Gantrez ES 425 by the company ISP, the copolymers of methacrylic acid and of methyl methacrylate sold under the name Eudragit L by the company Rohm Pharma, the copolymer of methacrylic acid and of ethyl acrylate sold under the name Luvimer MAEX by the company BASF, the terpolymer of vinylpyrrolidone/acrylic acid/lauryl methacrylate sold under the name Acrylidone LM by the company ISP, the vinyl acetate/crotonic acid copolymer sold under the name Luviset CA 66 by the company BASF and the vinyl acetate/crotonic acid/polyethylene glycol terporymer sold under the name Aristoflex A by the company BASF.

The anionic polymers more particularly preferred are chosen from vinyl acetate/vinyl tert-butyl benzoate/crotonic acid terpolymers, the monoesterified methyl vinyl ether/maleic anhydride copolymer sold under the name Gantrez ES 425 by the company ISP, the copolymers of methacrylic acid and of methyl methacrylate sold under the name Eudragit L by the company Rohm Pharma, the copolymer of methacrylic acid and of ethyl acrylate sold under the name Luvimer MAEX by the company BASF and the terpolymer of vinylpyrrolidone/acrylic acid/lauryl methacrylate sold under the name Acrylidone LM by the company ISP.

According to the invention, anionic polymers in latex or pseudolatex form, that is to say in the form of a dispersion of insoluble polymer particles, can also be used.

The cationic polymers which can be used in accordance with the present invention can be chosen from all of those already known per se, in particular those described in patent application EP-A-0,337,354 and in French patent applications FR-A-2,270,846, 2,383,660, 2,598,611, 2,470,596 and 2,519,863.

Even more generally, for the purposes of the present invention, the expression "cationic polymer" denotes any polymer containing cationic groups or groups that can be ionized into cationic groups.

The preferred cationic polymers are chosen from those which contain units containing primary, secondary, tertiary and/or quaternary amine groups which can either form part of the main polymer chain or can be borne by a side substituent which is directly connected to this main polymer chain.

The cationic polymers used generally have a molecular mass of approximately between 500 and $5 \times 10^6$ and preferably approximately between $10^3$ and $3 \times 10^6$.

Among the cationic polymers, mention may be made more particularly of cuaternized proteins (or protein hydrolysates) and polymers of the polyamine, polyamino amide and quaternary polyammonium type. These are known products.

The quaternized protein or protein hydrolysates are, in particular, chemically modified polypeptides bearing quaternary ammonium groups at the end of the chain or grafted thereto. Their molecular mass can vary, for example, from 1500 to 10,000 and in particular approximately from 2000 to 5000. Among these compounds, mention may be made in particular of:

collagen hydrolysates bearing triethylammonium groups, such as the products sold under the name "Quat-Pro E" by the company Maybrook and referred to in the CTFA dictionary as "Triethonium hydrolysed collagen ethosulphate";

collagen hydrolysates bearing trimethylammonium and trimethylstearylammonium chloride groups, sold under the name "Quat-Pro S" by the company Maybrook and referred to in the CTFA dictionary as "Steartrimonium hydrolysed collagen";

protein hydrolysates bearing, on the polypeptide chain, quaternary ammonium groups containing at least one alkyl radical having from 1 to 18 carbon atoms.

Among these protein hydrolysates, mention may be made, inter alia, of:

"Croquat L" whose quaternary ammonium groups ontain a $C_{12}$ alkyl group;

"Croquat M" whose quaternary ammonium groups ontain $C_{10}$–$C_{18}$ alkyl groups;

"Croquat S" whose quaternary ammonium groups contain a $C_{18}$ alkyl group;

"Crotein Q" whose quaternary ammonium groups contain at least one alkyl group having from 1 to 18 carbon atoms.

These various products are sold by the company Croda.

Other quaternized proteins or protein hydrolysates are, for example, those corresponding to the formula:

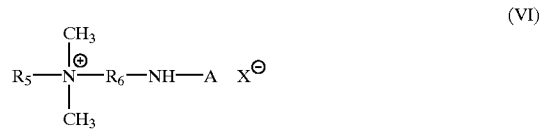

(VI)

in which X⁻ is an anion of an organic or inorganic acid, A denotes a protein residue derived from collagen protein hydrolysates, $R_5$ denotes a lipophilic group containing up to 30 carbon atoms and $R_6$ represents an alkylene group having from 1 to 6 carbon atoms. Mention may be made, for example, of the products sold by the company Inolex under the name "Lexein QX 3000", referred to in the CTFA dictionary as "Cocotrimonium collagen hydrolysate".

Mention may also be made of quaternized plant proteins, such as wheat, corn or soya proteins: as quaternized wheat proteins, mention may be made of those sold by the company Croda under the names "Hydrotriticum WQ or QM", referred to in the CTFA dictionary as "Cocodimonium hydrolysed wheat protein", "Hydrotriticum QL" referred to in the CTFA dictionary as "Lauridimonium hydrolysed wheat protein" or alternatively "Hydrotriticum QS" referred to in the CTFA dictionary as "Steardimonium hydrolysed wheat proteins".

Another family of cationic polymers is that of silicone cationic polymers. Among these polymers, mention may be made of:

(a) the silicone polymers corresponding to formula (VII) below:

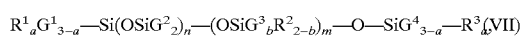

in which:
$G^1$, $G^2$, $G^3$ and $G^4$, which may be identical or different, denote a hydrogen atom or a phenyl, OH, $C_1$–$C_{18}$ alkyl, for example methyl, $C_2$–$C_{18}$ alkenyl or $C_1$–$C_{18}$ alkoxy group,
a and a', which may be identical or different, denote the number 0 or an integer from 1 to 3, in particular
b denotes 0 or 1, and in particular 1,
m and n are numbers such that the sum (n+m) can vary especially from 1 to 2000 and in particular from 50 to 150, it being possible for n to denote a number from 0 to 1999 and in particular from 49 to 149 and for m to denote a number from 1 to 2000 and in particular from 1 to 10;

$R^1$, $R^2$, $R^3$, and $R^4$, which may be identical or different, denote a monovalent radical of formula $-C_qH_{2q}O_sR^5_tL$ in which q is a number from 1 to 8, s and t, which may be identical or different, are equal to 0 or 1, $R^5$ denotes an optionally hydroxylated alkylene group and L is an optionally quaternized amine group chosen from the groups:

—NR"—$CH_2$—$CH_2$—N'(R")$_2$
—N(R")$_2$
—N$^\oplus$(R")$_3$A$^-$
—N$^\oplus$H(R")$_2$A$^-$
—N$^\oplus$H$_2$(R")A$^-$
—N(R")—$CH_2$—$CH_2$—N$^\oplus$R"H$_2$A$^-$, in which R" can denote hydrogen, phenyl, benzyl or a saturated monovalent hydrocarbon radical, for example an alkyl radical having from 1 to 20 carbon atoms, and A$^-$ represents a halide ion such as, for example, fluoride, chloride, bromide or iodide.

Products corresponding to this definition are, for example, the polysiloxanes referred to in the CTFA dictionary as "amodimethicone" and corresponding to formula (VIII) below:

(VIII)

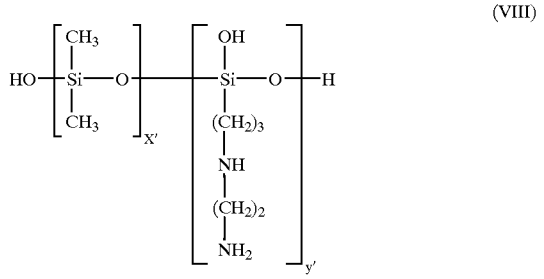

in which x' and y' are integers dependent on the molecular weight, generally such that the said molecular weight is approximately between 5000 and 20,000.

A product corresponding to formula (VIII) is the polymer referred to in the CTFA dictionary as "trimethylsilylamodimethicone", corresponding to the formula:

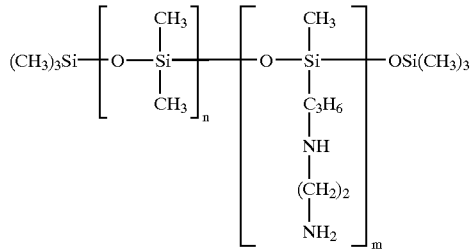

in which n and m have the meanings given above (cf. formula VIII).

A commercial product corresponding to this definition is a mixture (90/10 by weight) of a polydimethylsiloxane containing aminoethyl aminoisobutyl groups and of a polydimethylsiloxane sold under the name Q2-8220 by the company Dow Corning.

Such polymers are described, for example, in patent application EP-A-95,238.

Other polymers corresponding to formula (VIII) are the silicone polymers corresponding to the following formula:

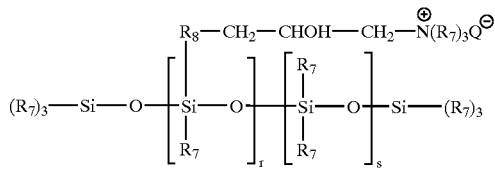

in which:

$R^7$ represents a monovalent hydrocarbon radical having from 1 to 18 carbon atoms, and in particular a $C_1$–$C_{18}$ alkyl or $C_2$–$C_{18}$ alkenyl radical, for example methyl;

$R_8$ represents a divalent hydrocarbon radical, in particular a $C_1$–$C_{18}$ alkylene radical or a divalent $C_1$–$C_{18}$, for example $C_1$–$C_8$ alkyleneoxy radical;

$Q^-$ is a halide ion, in particular chloride;

r represents an average statistical value from 2 to 20 and in particular from 2 to 8;

s represents an average statistical value from 20 to 200 and in particular from 20 to 50.

Such polymers are described more particularly in U.S. Pat. No. 4,185,087.

b—the compounds of formula:

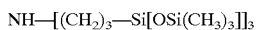

corresponding to the CTFA name "aminobispropyldimethicone".

A polymer falling within this category is the polymer sold by the company Union Carbide under the name "Ucar Silicone ALE 56".

When these silicone polymers are used, a particularly advantageous embodiment is their joint use with cationic and/or nonionic surfactants. It is possible to use, for example, the product sold under the name "Emulsion Cationic DC 929" by the company Dow Corning, which comprises, besides amodimethicone, a cationic surfactant comprising a mixture of products corresponding to the formula:

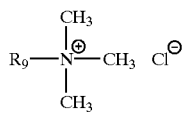

in which $R_9$ denotes alkenyl and/or alkyl radicals having from 14 to 22 carbon atoms, fatty acid derivatives of tallow, in combination with a nonionic surfactant of formula:

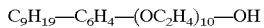

known under the name "Nonoxynol 10".

Another commercial product which can be used according to the invention is the product sold under the name "Dow Corning Q2 7224" by the company Dow Corning, containing, in combination with the trimethylsilylamodimethicone of formula (IV), a nonionic surfactant of formula: $C_8H_{17}$—$C_6H_4$—$(OCH_2CH_2)_n$—OH where n=40, also known as octoxynol-40, another nonionic surfactant of formula: $C_{12}H_{25}$—$(OCH_2$—$CH_2)_n$—OH where n=6, also known as isolaureth-6, and glycol.

The polymers of the quaternary polyammonium polyamino amide and polyamine type which can be used in accordance with the present invention and which may be mentioned in particular are those described in French patents Nos. 2,505,348 or 2,542,997. Among these polymers, mention may be made of:

(1) Quaternized or non-quaternized vinylpyrrolidone/ dialkylaminoalkyl acrylate or methacrylate copolymers, such as the products sold under the name "Gafquat" by the company ISP such as, for example, Gafquat 734, 755 or HS100 or alternatively the product known as "Copolymer 937". These polymers are described in detail in French patents 2,077,143 and 2,393,573.

(2) The cellulose ether derivatives containing quaternary ammonium groups, described in French patent 1,492,597, and in particular polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The commercial products corresponding to this definition are more particularly the products sold under the names "Celquat L 200" and "Celquat H 100" by the company National Starch.

(4) The cationic polysaccharides described more particularly in U.S. Pat. No. 3,589,578 and 4,031,307 and more particularly the product marketed under the name "Jaguar C.13 S" sold by the company Meyhall.

(5) Polymers consisting of piperazinyl units and of divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, in particular, in French patents 2,162,025 and 2,280,361;

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent is used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2,252,840 and 2,368,508;

(7) The polyamino amidederivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical contains from 1 to 4 carbon atoms and preferably denotes methyl, ethyl or propyl. Such polymers are described in particular in French patent 1,583,363.

Among these derivatives, mention may be made more particularly of the adipic acid/ dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/ epoxypropyl/diethylenetriamine copolymer.

(9) Cyclopolymers of methyldiallylamine or of thyldiallylammonium, such as the polymers containing, as chain constituent, units corresponding to formula (IX) or (IX'):

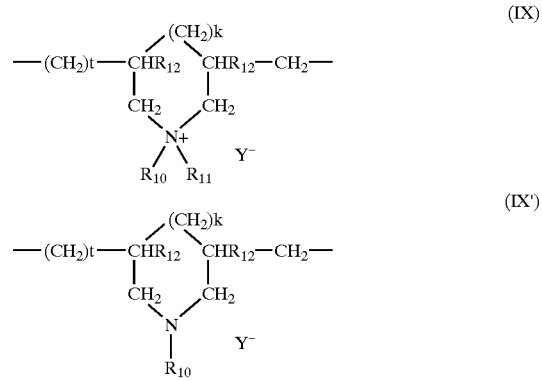

in which formulae k and t are equal to 0 or 1, the sum k+t being equal to 1; $R_{12}$ denotes a hydrogen atom or a methyl radical; $R_{10}$ and $R_{11}$ independently of each other, denote an alkyl group having from 1 to 22 carbon atoms, a hydroxyalkyl group in which the alkyl group preferably has 1 to 5 carbon atoms, or a lower amidoalkyl group, or $R_{10}$ and $R_{11}$ can denote, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate or phosphate. These polymers are described in particular in French patent 2,080,759 and in its Certificate of Addition 2,190,406.

Among the polymers defined above, mention may be made more particularly of the dimethyldiallylammonium chloride homopolymer sold under the name "Merquat 100" by the company Merck and the copolymers of dimethyldiallylammonium chloride and of acrylamide, sold under the name "Merquat 550".

(10) The quaternary diammonium polymer containing repeating units corresponding to the formula:

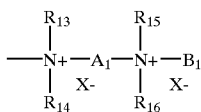

(X)

in which:
- $R_{13}$, $R_{14}$, $R_{15}$ and $R_{16}$ which may be identical or different, represent aliphatic, alicyclic or arylaliphatic radicals containing from 1 to 20 carbon atoms or lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$–$C_6$ alkyl radical substituted with a nitrile, ester, acyl or amide group or a group —CO—O—$R_{17}$—D or —CO—NH—$R_{17}$—D where $R_{17}$ is an alkylene and D is a quaternary ammonium group;
- $A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulphur atoms or sulphoxide, sulphone, disulphide, amino, alkylamino, hydroxyl, quaternary ammonium, ureido, amide or ester groups, and
- $X^-$ denotes an anion derived from an inorganic or organic acid;
- $A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group $(CH_2)_n$—CO—D—OC—$(CH_2)_n$— in which D denotes:
  a) a glycol residue of formula: —O—Z—O—, where Z denotes a linear or branched hydrocarbon radical or a group corresponding to one of the following formulae:

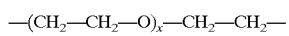

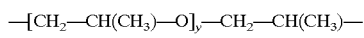

where x and y denote an integer from 1 to 4, representing a defined and unique degree of polymerization or any number from 1 to 4 representing an average degree of polymerization;
  b) a bis-secondary diamine residue such as a piperazine derivative;
  c) a bis-primary diamine residue of formula: —NH—Y—NH—, where Y denotes a linear or branched hydrocarbon radical, or alternatively the divalent radical

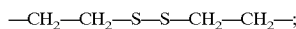

d) a ureylene group of formula: —NH—CO—NH—.

Preferably, $X^-$ is an anion such as chloride or bromide.

These polymers generally have a molecular mass of between 1000 and 100,000.

Polymers of this type are described in particular in French patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

(11) Quaternary polyammonium polymers consisting of units of formula (XI):

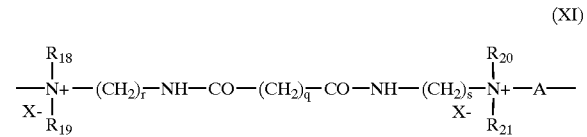

in which formula:
- $R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2$($OCH_2CH_2$)$_p$OH radical,
- where p is equal to 0 or to an integer between 1 and 6, with the proviso that $R_{18}$, $R_{19}$, $R_{20}$ and $R_{21}$ do not simultaneously represent a hydrogen atom,
- r and s, which may be identical or different, are integers between 1 and 6,
- q is equal to 0 or to an integer between 1 and 34,
- X denotes a halogen atom,
- A denotes a dihalide radical or preferably represents —$CH_2$—$CH_2$—O—$CH_2$—$CH_2$—.

Such compounds are described in particular in patent application EP-A-122,324.

Among these products, mention may be made, for example, of "Mirapol A 15", "Mirapol AD1", "Mirapol AZ1" and "Mirapol 175" sold by the company Mirapol.

(12) Homopolymers or copolymers derived from acrylic or methacrylic acid and containing units:

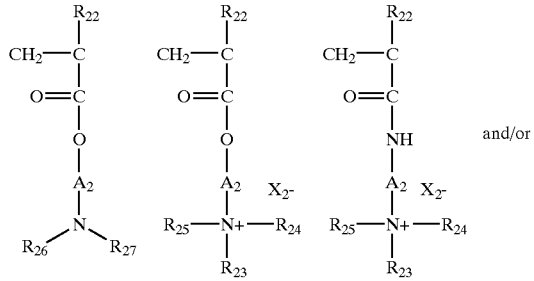

in which the groups $R_{22}$ independently denote H or $CH_3$, the groups $A_1$ independently denote a linear or branched alkyl group of 1 to 6 carbon atoms or a hydroxyalkyl group of 1 to 4 carbon atoms, the groups $R_{23}$, $R_{24}$ and $R_{25}$, which may be identical or different, independently denote an alkyl group of 1 to 18 carbon atoms or a benzyl radical, the groups $R_{26}$ and $R_{27}$ represent a hydrogen atom or an alkyl group of 1 to 6 carbon atoms, $X_2^-$ denotes an anion, for example methosulphate or halide, such as chloride or bromide.

The comonomer(s) which can be used in the preparation of the corresponding copolymers belong to the family of acrylamides, methacrylamides, diacetone acrylamides, acrylamides and methacrylamides substituted on the nitrogen with lower alkyls, alkyl esters, acrylic or methacrylic acids, vinylpyrrolidone or vinyl esters.

(13) Quaternary polymers of vinylpyrrolidone and of vinylimidazole, such as, for example, the products sold under the names Luviquat FC 905, FC 550 and FC 370 by the company BASF.

(14) Polyamines such as Polyquart H sold by Henkel under the reference name "Polyethylene glycol (15) tallow polyamine" in the CTFA dictionary.

(15) Crosslinked methacryloyloxyethyltrimethylammonium chloride polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethyl-ammonium chloride copolymer (20/80 by weight) in the form of a dispersion containing 50% by weight of the said copolymer in mineral oil can be used more particularly. This dispersion is sold under the name "Salcare SC 92" by the company Allied Colloids. A crosslinked methacryloyloxyethyltri-methylammonium chloride homopolymer containing about 50% by weight of the homopolymer in mineral oil can also be used. This dispersion is sold under the name "Salcare SC 95" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

According to the invention, polymers chosen from Mirapol, the compound of formula (X) in which $R_{13}$, $R_{14}$, $R_{15}$ and $R_{16}$ represent a methyl radical, $A_1$ represents a radical of formula $-(CH_2)_3-$ and $B_1$ represents a radical of formula $-(CH_2)_6-$ and $X^-$ represents a chloride anion (referred to hereinbelow as Mexomer PO) and the compound of formula (X) in which $R_{13}$ and $R_{14}$ represent an ethyl radical, $R_{15}$ and $R_{16}$ represent a methyl radical, $A_1$ and $B_1$ represent a radical of formula $-(CH_2)_3-$ and $X^-$ represents a bromide anion (referred to hereinbelow as Mexomer PAK) can be used more particularly.

Among all the cationic polymers which can be used in the context of the present invention, it is preferred to use quaternary cellulose ether derivatives such as the products sold under the name "JR 400 " by the company Union Carbide Corporation, cyclopolymers, in particular the copolymers of dimethyldiallylammonium chloride and of acrylamide having a molecular weight of greater than 500,000, sold under the names "Merquat 550" and "Merquat S" by the company Merck, cationic polysaccharides and more particularly the polymer sold under the name "Jaguar C13S" by the company Meyhall, and, lastly, cationic silicone polymers.

According to the invention, cationic polymers in latex or pseudolatex form, that is to say in the form of a dispersion of insoluble polymer particles, can also be used.

According to the invention, the anionic polymer(s) can represent from 0.01% to 20% by weight, preferably from 0.05% to 15% by weight and even more preferably from 0.1% to 10% by weight, relative to the total weight of the final composition.

According to the invention, the cationic polymer(s) can represent from 0.01% to 20% by weight, preferably from 0.05% to 15% by weight and even more preferably from 0.1% to 10% by weight, relative to the total weight of the final composition.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and ispropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of particles.

The composition of the invention can also contain at least one additive chosen from thickeners, fatty acid esters, fatty acid esters of glycerol, silicones, surfactants, fragrances, preserving agents, sunscreens, proteins, vitamins, polymers, plant, animal, mineral or synthetic oils or any other additive conventionally used in the cosmetic field.

These additives are present in the composition according to the invention in proportions which can range from 0 to 20% by weight relative to the total weight of the composition. The precise amount of each additive depends on its nature and is determined readily by those skilled in the art.

Needless to say, a person skilled in the art will take care to select the optional compounds) to be added to the composition according to the invention such that the advantageous proper ties intrinsically associated with the composition in accordance with the invention are not, or are not substantially, adversely affected by the addition envisaged.

The compositions according to the invention can be in the form of a gel, a milk, a cream, a relatively thickened lotion or a foam.

The compositions of the invention a re used as rinse-out products or as leave-in products in particular to wash, care for, condition, maintain the style o f or shape keratin substances such as the hair.

These compositions are more particularly styling products such as hairsetting lotions, blow-drying lotions, fixing compositions (lacquers) and styling compositions. The lotions can be packaged in various forms, in particular in vapourizers, pump-dispenser bottles or in aerosol containers in order to ensure application of the composition in vapourized form or in the form of a foam. Such packaging forms are indicated, for example, when it is desired to obtain a spray, a lacquer or a foam for fixing or treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol foam, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, aland mixtures thereof, can also be used as propellant.

Another subject of the invention is a process for treating keratin substances such as the hair, which consists in applying a composition as defined above to the hair and then optionally in rinsing with water.

The invention will now be illustrated more fully with the aid of the examples which follow, which should not be considered as limiting it to the embodiments described. In the text which follows, AM means active material.

EXAMPLE 1

A styling foam of the following composition was prepared:

| | |
|---|---|
| grafted silicone polymer of formula (IV) of polymethyl/methylsiloxane structure containing 3-propylthio polymethacrylic acid groups and 3-propylthio polymethyl methacrylate groups | 0.55 g |
| monoesterified methyl vinyl ether/maleic anhydride copolymer sold by the company ISP under the name Gantrez ES 425 | 0.55 gAM |
| copolymer of hydroxyethylcellulose and of diallyldimethylammonium chloride, sold under the trade name Celquat L200 by the company National Starch | 0.55 g |
| aminomethylpropanol    qs | pH 7.5 |
| ethanol | 11.1 g |
| demineralized water    qs | 100 g |
| Pressurization schema: | |
| Above composition: | 90 g |
| Ternary mixture of n-butane, isobutane and propane (23/55/22), sold under the name "Aerogaz 3.2 N" by the company Elf Aquitaine | 10 g |

EXAMPLE 2

A styling gel of the following composition was prepared:

| | |
|---|---|
| grafted silicone polymer of formula (IV) of polymethyl/methylsiloxane structure containing 3-propylthio polymethacrylic acid groups and 3-propylthio polymethyl methacrylate groups | 0.5 g |
| methacrylic acid/methyl methacrylate copolymer as an aqueous-alcoholic solution (10°) containing 21% AM | 0.5 gAM |
| copolymer of hydroxyethylcellulose and of diallyldimethylammonium chloride, sold under the trade name Celquat L200 by the company National Starch | 0.5 g |
| aminomethylpropanol    qs | pH 7.5 |
| ethanol | 10 g |
| demineralized water    qs | 100 g |

What is claimed is:

1. A cosmetic or dermatological composition consisting essentially of cosmetically or dermatologically acceptable medium,
   (a) at least one grafted silicone polymer comprising:
      a polysiloxane portion and
      a portion comprising a non-silicone organic chain, wherein one of the two portions constitutes the main chain of said at least one grafted silicone polymer, and the other is grafted onto said main chain, and
   (b) at least one combination of at least one anionic polymer and at least one cationic polymer, wherein said (b) differs from said (a).

2. A cosmetic or dermatological composition according to claim 1, wherein said composition is a treatment composition for a keratin substance.

3. A cosmetic or dermatological composition according to claim 2, wherein said keratin substance is human hair.

4. A Cosmetic or dermatological composition according to claim 1, wherein said at least one grafted silicone polymer is selected from polymers having a non-silicone organic skeleton grafted with at least one monomer containing at least one polysiloxane and polymers having a polysiloxane skeleton grafted with at least one non-silicone organic monomer.

5. A cosmetic or dermatological composition according to claim 1, wherein said at least one grafted silicone polymer contains a non-silicone organic skeleton comprising an organic main chain formed from at least one organic monomer containing no silicone, and further wherein on said organic main chain is grafted, inside said chain and optionally on at least one of the ends of said chain, at least one polysiloxane monomer.

6. A cosmetic or dermatological composition according to claim 4, wherein said at least one non-silicone organic monomers constituting the main chain of said at least one grafted silicone polymer is selected from monomers containing ethylenic unsaturation which are polymerizable via a radical route, monomers which are polymerizable by polycondensation and monomers which involve ring opening.

7. A cosmetic or dermatological composition according to claim 1, wherein said at least one grafted silicone polymer comprises:
   a) from 0 to 98% by weight of at least one lipophilic monomer (A) of low polarity containing ethylenic unsaturation of low polarity, which is polymerizable via a radical route;
   b) from 0 to 98% by weight of at least one polar hydrophilic monomer (B) containing ethylenic unsaturation, which is copolymerizable with said (A) monomer(s);
   c) from 0.01 to 50% by weight of at least one polysiloxane macromer (C) of formula (I):

$$X(Y)_n Si(R)_{3-m} Z_m \qquad (I)$$

in which:
   X denotes a vinyl group which is copolymerizable with the monomers (A) and (B);
   Y denotes a divalent bonding group;
   R denotes a hydrogen, a $C_1$–$C_8$ alkyl or alkoxy or a $C_6$–$C_{12}$ aryl,
   Z denotes a monovalent polysiloxane unit having a number-average molecular weight of at least 500;
   n is 0 or 1 and m is an integer ranging from 1 to 3;
   wherein the percentages are calculated relative to the total weight of the monomers (A), (B) and (C) and wherein the sum of a) and b) cannnot constitute 0% by weight relative to the total weight of the monomers.

8. A cosmetic or dermatological composition according to claim 7, wherein said at least one lipophilic monomer (A) is an acrylic or methacrylic acid ester of a $C_1$–$C_{18}$ alcohol; styrene; a polystyrene macromer; vinyl acetate; vinyl propionate; α-methylstyrene; tert-butylstyrene; butadiene; cyclohexadiene; ethylene; propylene; vinyltoluene; an acrylic or methacrylic acid ester of a 1,1-dihydroperfluoroalkanol or a homologue thereof; an acrylic or methacrylic acid ester of a ω-hydridofluoroalkanol; an acrylic or methacrylic acid ester of a fluoroalkylsulphoamido alcohol; an acrylic or methacrylic acid ester of a fluoroalkyl alcohol; or an acrylic or methacrylic acid ester of a fluoroether alcohol.

9. A cosmetic or dermatological composition according to claim 8, wherein said at least one lipophilic monomer (A) is n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)ethyl acrylate or 2-(N-butylperfluorooctanesulphonamido)ethyl acrylate.

10. A cosmetic or dermatological composition according to claim 7, wherein said at least one polar hydrophilic monomer (B) is acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride or demiesters thereof, hydroxyalkyl (meth)acrylate, diallyidimethylammonium chloride, vinylpyrrolidone, vinyl ether, maleimide, vinylpyridine, vinylimidazole, a heterocyclic vinyl polar compound, styrene sulphonate, allyl alcohol, vinyl alcohol or vinyl caprolactam.

11. A cosmetic or dermatological composition according to claim 10, wherein said at least one polar hydrophilic monomer (B) is acrylic acid, N',N-dimethylacrylamide, dimethylaminoethyl methacrylate, quaternized dimethylaminoethyl methacrylate or vinylpyrrolidone.

12. A cosmetic or dermatological composition according to claim 7, wherein said at least one polysiloxane macromer (C) is a compound corresponding to formula (II):

$$CHR^1=CR^2-\overset{O}{\overset{\|}{C}}-O-(CH_2)_q-(O)_p-Si(R^3)_{3-m}(O-\underset{CH_3}{\overset{CH_3}{\underset{|}{\overset{|}{Si}}}})_r-R^4 \quad (II)$$

in which:

$R^1$ is hydrogen or —COOH;

$R^2$ is hydrogen, methyl or —CH$_2$COOH;

$R^3$ is $C_1$–$C_6$ alkyl, alkoxy, or alkylamino, $C_6$–$C_{12}$ aryl or hydroxyl;

$R^4$ is $C_1$–$C_6$ alkyl, alkoxy or alkylamino, $C_6$–$C_{12}$ aryl or hydroxyl;

q is an integer from 2 to 6;

p 0 is or 1;

r is an integer front 5 to 700;

m is an integer from 1 to 3.

13. A cosmetic or dermatological composition according to claim 12, wherein $R^1$ is hydrogen.

14. A cosmetic or dermatological composition according to claim 12, wherein $R^2$ is methyl.

15. A cosmetic or dermatological composition according to claim 12, wherein $R^3$ is methyl.

16. A cosmetic or dermatological composition according to claim 12, wherein $R^4$ is methyl.

17. A cosmetic or dermatological composition according to claim 12, wherein q is 3.

18. A cosmetic or dermatological composition according to claim 12, wherein m is 1.

19. A cosmetic or dermatological composition according to claim 7, wherein said at least one polysiloxane macromer (C) is a compound corresponding to the following formula:

$$CH_2=\underset{CH_3}{\overset{|}{C}}-\overset{O}{\overset{\|}{C}}-O-(CH_2)_3-\underset{CH_3}{\overset{CH_3}{\underset{|}{\overset{|}{Si}}}}-O-\left[\underset{CH_3}{\overset{CH_3}{\underset{|}{\overset{|}{Si}}}}-O\right]_n-\underset{CH_3}{\overset{CH_3}{\underset{|}{\overset{|}{Si}}}}-(CH_2)_3-CH_3$$

in which n is an integer ranging from 5 to 700.

20. A cosmetic or dermatological composition according to claim 1, wherein said at least one grafted silicone polymer contains at least one copolymer which may be obtained by radical polymerization of a monomer mixture comprising:

a) 60% by weight of tert-butyl acrylate;

b) 20% by weight of acrylic acid; and c) 20% by weight of silicone macromer of formula:

$$CH_2=\underset{CH_3}{\overset{|}{C}}-\overset{O}{\overset{\|}{C}}-O-(CH_2)_3-\underset{CH_3}{\overset{CH_3}{\underset{|}{\overset{|}{Si}}}}-O-\left[\underset{CH_3}{\overset{CH_3}{\underset{|}{\overset{|}{Si}}}}-O\right]_n-\underset{CH_3}{\overset{CH_3}{\underset{|}{\overset{|}{Si}}}}-(CH_2)_3-CH_3$$

in which:

n is an integer ranging from 5 to 700;

wherein the weight percentages are calculated relative to the total weight of said monomer mixture.

21. A cosmetic or dermatological composition according to claim 1, wherein said at least one grafted silicone polymer is at least one copolymer which may be obtained by radical polymerization of a monomer mixture comprising:

a) 80% by weight of tert-butyl acrylate; and b) 20% by weight of silicone macromer of formula:

$$CH_2=\underset{CH_3}{\overset{|}{C}}-\overset{O}{\overset{\|}{C}}-O-(CH_2)_3-\underset{CH_3}{\overset{CH_3}{\underset{|}{\overset{|}{Si}}}}-O-\left[\underset{CH_3}{\overset{CH_3}{\underset{|}{\overset{|}{Si}}}}-O\right]_n-\underset{CH_3}{\overset{CH_3}{\underset{|}{\overset{|}{Si}}}}-(CH_2)_3-CH_3$$

in which:

n is an integer ranging from 5 to 700;

wherein the weight percentages are calculated relative to the total weight of said monomer mixture.

22. A cosmetic or dermatological composition according to claim 4, wherein said polymers containing a non-silicone organic skeleton grafted with at least one monomer containing at least one polysiloxane have a number-average molecular weight ranging from 10,000 to 2,000,000 and a glass transition temperature Tg or a crystalline melting point Tm of at least –20° C.

23. A cosmetic or dermatological composition according to claim 5, wherein said composition comprises at least one polymer containing a non-silicone organic skeleton grafted with at least one monomer containing at least one polysiloxane, wherein said at least one polymer is obtained by reactive extrusion of a polysiloxane macromer having a terminal reactive function, with a polyolefin polymer containing reactive groups which can react with the reactive terminal function of said at least one polysiloxane macromer to form a covalent bond resulting in a grafting of said polysiloxane macromer to said polyolefin polymer, said polyotefin polymer forming the skeleton of said polymers.

24. A cosmetic or dermatological composition according to claim 23, wherein said polyolefin polymer is selected from polyethylenes and polymers of ethylene-derived monomers containing reactive functions which can react with the terminal function of the polysiloxane macromer.

25. A cosmetic or dermatological composition according to claim 24, wherein said polyolefin polymer is a copolymer of
(a) ethylene and/or of ethylene derivatives and of
(b) monomers which are monomers containing a carboxylic function; monomers containing an acid anhydride function; monomers containing an acid chloride function; monomers containing an ester function; or monomers containing an isocyanate function.

26. A cosmetic or dermatological composition according to claim 23, herein said at least one polysiloxane macromer is a polysiloxane containing a functionalized group, at the end of the polysiloxane chain or close to the end of said chain, said functionalized group being an alcohol, thiol, epoxy group or a primary or secondary amine.

27. A cosmetic or dermatological composition according to claim 23, wherein said at least one polysiloxane macromer is a polysiloxane corresponding to formula (III):

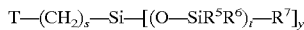

$$T-(CH_2)_s-Si-[(O-SiR^5R^6)_t-R^7]_y \quad (II)$$

in which:
T is an $NH_2$, NHR', an epoxy, OH, or a SH function;
$R^5$, $R^6$, $R^7$ and R' each independently denotes a $C_1$–$C_6$ alkyl, phenyl, benzyl, $C_6$–$C_{12}$ alkylphenyl or hydrogen;
s is a number ranging from 2 to 100;
t is a number ranging from 0 to 1000; and
y is a number ranging from 1 to 3.

28. A cosmetic or dermatological composition according to claim 27, wherein said at least one polysiloxane macromer has a number-average molecular weight ranging from 5,000 to 300,000.

29. A cosmetic or dermatological composition according to claim 1, wherein said composition comprises at least one grafted silicone polymer containing a polysiloxane main chain grafted with at least one non-silicone organic monomer wherein on said a polysiloxane main chain is grafted, inside said main chain and optionally on at least one of its ends, said at least one non-silicone organic monomer.

30. A cosmetic or dermatological composition according to claim 29, wherein at least one grafted silicone polymer is obtained by radical copolymerization between:
at least one non-silicone organic monomer having ethylenic unsaturation which is an anionic or hydrophobic monomer, and,
at least one polysiloxane having in its chain at least one functional group capable of reacting with said ethylenic unsaturation of said at least one non-silicone organic monomer.

31. A cosmetic or dermatological composition according to claim 30, wherein said polysiloxane has several functional groups in its chain capable of reacting with said ethylenic unsaturation of said at least one non-silicone organic monomer.

32. A cosmetic or dermatological composition according to claim 30, wherein said non-silicone anionic organic monomer is acrylic acid, methacrylic acid, maleic acid, maleic anhydride, itaconic acid, fumaric acid and crotonic acid, an alkali-metal salt of said acids, an alkaline-earth metal salt of said acids, or an ammonium salt of aid acids.

33. A cosmetic or dermatological composition according to claim 30, wherein said non-silicone hydrophobic organic monomer is an acrylic acid ester of an alkanol or a methacrylic acid ester of an alkanol.

34. A cosmetic or dermatological composition according to claim 33, wherein said alkanol is $C_1$–$C_{18}$.

35. A cosmetic or dermatological composition according to claim 34, wherein said alkanol is $C_1$–$C_{12}$.

36. A cosmetic or dermatological composition according to claim 30, wherein said non-silicone hydrophobic organic monomer is an isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate or a stearyl (meth)acrylate.

37. A cosmetic or dermatological composition according to claim 29, wherein said at least one grafted silicone polymer comprises, on the main silicone chain, at least one non-silicone organic group of anionic nature obtained by the radical (homo)polymerization of at least one non-silicone anionic unsaturated carboxylic acid monomer partially or totally neutralized in the form of a salt.

38. A cosmetic or dermatological composition according to claim 29, wherein said at least one grafted silicone polymer is a silicone polymer containing in its structure at least one unit of formula (IV):

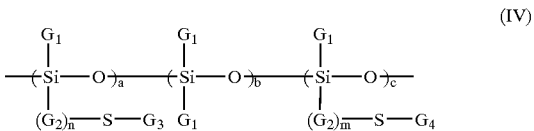

(IV)

in which:
the radicals $G_1$ each independently represent hydrogen, a $C_1$–$C_{10}$ alkyl radical or a phenyl radical;
the radicals $G_2$ each independently represent a divalent $C_1$–$C_{10}$ alkylene group;
$G_3$ represents a polymer residue resulting from the (homo)polymerization of at least one anionic monomer containing ethylenic unsaturation;
$G_4$ represents a polymer residue resulting from the (homo)polymerization of at least one hydrophobic monomer containing ethylenic unsaturation;
m and n are equal to 0 or 1;
a is an integer ranging from 0 to 50;
b is an integer ranging from 10 to 350;
c is an integer ranging from 0 to 50;
with the proviso that one of a and c is not 0.

39. A cosmetic or dermatological composition according to claim 38, wherein said at least one unit of formula (IV) has at least one of the following characteristics:
the radicals $G_1$ denote a $C_1$–$C_{10}$ alkyl radical;
n is 1;
the radicals $G_2$ represent a divalent $C_1$–$C_3$ radical;
$G_3$ represents a polymeric residue resulting from the (homo)polymerization of at least one carboxylic acid monomer containing ethylenic unsaturation; and
$G_4$ represents a polymeric residue resulting from the (homo)polymerization of at least one $C_1$–$C_{10}$ alkyl (meth)acrylate monomer.

40. A cosmetic or dermatological composition according to claim 38, wherein said at least one unit of formula (IV) simultaneously has the following characteristics:
the radicals $G_1$ each denotes a methyl radical;
n is 1;
the radicals $G_2$ each represents a propylene radical;
$G_3$ represents a polymeric residue resulting from the (homo)polymerization of at least one monomer which is an acrylic acid or a methacrylic acid; and G₄ represents a polymeric residue resulting from the (homo)polymerization of at least one monomer which is an isobutyl or methyl (meth)acrylate monomers.

41. A cosmetic or dermatological composition according to claim 29, wherein said at least one grafted silicone polymer has a number-average molecular mass ranging from 10,000 to 100,000.

42. A cosmetic or dermatological composition according to claim 41, wherein said at least one grafted silicone polymer has a number-average molecular mass ranging from 10,000 to 100,000.

43. A cosmetic or dermatological composition according to claim 1, wherein said at least one grafted silicone polymer is present in a concentration ranging from 0.01 to 20% by weight relative to the total weight of the composition.

44. A cosmetic or dermatological composition according to claim 43, wherein said at least one grafted silicone polymer is present in a concentration ranging from 0.1 to 15% by weight relative to the total weight of the composition.

45. A cosmetic or dermatological composition according to claim 44, wherein said at least one grafted silicone polymer is present in a concentration ranging from 0.5 to 10% by weight relative to the total weight of the composition.

46. A cosmetic or dermatological composition according to claim 1, wherein said at least one anionic polymer is selected from:

acrylic acid copolymers;

copolymers derived from crotonic acid;

polymers derived from maleic, fumaric or itaconic acid or anhydride with vinyl esters, vinyl-ethers, vinyl halides, phenylvinyl derivatives, acrylic acid and its esters;

copolymers of methacrylic acid and of methyl methacrylate; and the copolymer of methacrylic acid and of ethyl acrylate.

47. A cosmetic or dermatological composition according to claim 1, wherein said at least one cationic polymer is a quaternary cellulose ether derivative, a copolymer of cellulose with a water-soluble quaternary ammonium monomer, a cyclopolymer, a cationic polysaccharide, a cationic silicone polymer, a quaternized or non-quaternized vinylpyrrolidone/dialkylaminoalkyl acrylate or methacrylate copolymer, a quaternary polymer of vinylpyrrolidone or a quaternary polymer of vinylimidazole.

48. A cosmetic or dermatological composition according to claim 1, wherein said at least one anionic polymer is present in a concentration ranging from 0.01 to 20% by weight relative to the total weight of the composition.

49. A cosmetic or dermatological composition according to claim 48, wherein said at least one anionic polymer is present in a concentration ranging from 0.05 to 15% by weight relative to the total weight of the composition.

50. A cosmetic or dermatological composition according to claim 49, wherein said at least one anionic polymer is present in a concentration ranging from 0.1 to 10% by weight relative to the total weight of the composition.

51. A cosmetic or dermatological composition according to claim 1, wherein said at least one cationic polymer is present in a concentration ranging from 0.01 to 20% by weight relative to the total weight of the composition.

52. A cosmetic or dermatological composition according to claim 51, wherein said at least one cationic polymer is present in a concentration ranging from 0.05 to 15% by weight relative to the total weight of the composition.

53. A cosmetic or dermatological composition according to claim 52, wherein said at least one cationic polymer is present in a concentration ranging from 0.1 to 10% by weight relative to the total weight of the composition.

54. A cosmetic or dermatological composition according to claim 1, wherein said composition further comprises at least one additive which is a thickener, fatty acid ester, fatty acid ester of glycerol, silicone, surfactant, fragrance, preserving agent, sunscreen, protein, vitamin, different polymer, plant, animal, mineral or synthetic oil or any other suitable cosmetic additive.

55. A cosmetic or dermatological composition according to claim 1, wherein said cosmetically or dermatologically acceptable medium comprises water or a mixture of water and at least one second cosmetically acceptable solvent.

56. A cosmetic or dermatological composition according to claim 1, wherein said at least one grafted silicone polymer is dissolved in the cosmetically or dermatologically acceptable medium or is in the form of an aqueous dispersion of particles.

57. A cosmetic or dermatological composition according to claim 1 wherein said composition is in the form of a gel, a milk, a cream, a thickened lotion or a foam.

58. A cosmetic or dermatological composition according to claim 1, wherein said composition is a hair product.

59. A cosmetic or dermatological composition according to claim 1, wherein said hair product is a shampoo or a rinse-out or leave-in hair product applied before or after shampooing, dyeing, bleaching, permanent-waving or straightening the hair.

60. A cosmetic or dermatological composition according to claim 1, wherein said composition is packaged in the form of a vaporizer, pump-dispenser bottle or an aerosol container.

61. A process for treating a keratin substance comprising applying a composition according to claim 1 to said keratin substance and then optionally rinsing with water.

62. A process according to claim 60, wherein said keratin substance is human hair.

63. A cosmetic or dermatological composition according to claim 46, wherein said at least one anionic polymer is:

a vinylpyrrolidone/acrylic acid/lauryl methacrylate terpolymer;

a vinyl acetate/crotonic acid copolymer; or a vinyl acetate/crotonic acid/polyethylene glycol terpolymer.

* * * * *

UNITED STATES PATENT AND TRADEMARK OFFICE
CERTIFICATE OF CORRECTION

PATENT NO. : 6,471,952 B1
DATED : October 29, 2002
INVENTOR(S) : Claude Dubief, Daniele Cauwet-Martin and Christine Dupuis It is certified that error appears in the above-identified patent and that said Letters Patent is hereby corrected as shown below:

Title page,
Item [57], ABSTRACT,
Line 3, "as least" should read -- at least --.
Line 4, "grafter" should read -- grafted --.

Column 19,
Line 54, after "of" insert -- , in a --.

Column 20,
Line 3, "Cosmetic" should read -- cosmetic --.
Line 16, "monomer" should read -- macromer --.
Line 18, "claim 4" should read -- claim 5 --.

Column 21,
Line 14, "diallyidimethylammonium" should read -- diallyldimethylammonium --.
Line 21, "N',N-dimethylacrylamide" should read -- N,N-dimethylacrylamide --.
Line 48, "0 is" should read -- is 0 --.
Line 49, "front" should read -- from --.

Column 22,
Line 62, "polyotefin" should read -- polyolefin --.

Column 23,
Line 11, "herein" should read -- wherein --.
Line 20, "(II)" should read -- (III) --.
Line 61, "aid" should read -- said --.

Column 25,
Line 3, "monomers" should read -- monomer --.
Line 7, "100,000" should read -- 1,000,000 --.
Line 33, "vinyl-ethers" should read -- vinyl ethers --.

UNITED STATES PATENT AND TRADEMARK OFFICE
CERTIFICATE OF CORRECTION

PATENT NO.    : 6,471,952 B1
DATED         : October 29, 2002
INVENTOR(S)   : Claude Dubief, Daniele Cauwet-Martin and Christine Dupuis It is certified that error appears in the above-identified patent and that said Letters Patent is hereby corrected as shown below:

Column 26,
Line 47, "claim 60" should read -- claim 61 --.

Signed and Sealed this

First Day of April, 2003

JAMES E. ROGAN
*Director of the United States Patent and Trademark Office*